United States Patent [19]

Hamill

[11] 3,975,405

[45] Aug. 17, 1976

[54] MONOPHOSPHATE SALT OF o-CRESOLPHTHALEIN

[75] Inventor: Thomas E. Hamill, Fort Lauderdale, Fla.

[73] Assignee: Coulter Diagnostics, Inc., Hialeah, Fla.

[22] Filed: Aug. 1, 1974

[21] Appl. No.: 493,775

[52] U.S. Cl. ................... 260/343.4; 195/103.5 R
[51] Int. Cl.² ................... C07D 307/94; C12K 1/04
[58] Field of Search ................... 260/343.4

[56] References Cited
UNITED STATES PATENTS 3,331,857   7/1967   Coleman ........................ 260/343.4
3,331,862   7/1967   Merrill et al. ..................... 260/396
3,466,306   9/1969   Babson .......................... 260/395

*Primary Examiner*—Anton H. Sutto
*Attorney, Agent, or Firm*—Silverman & Cass, Ltd.

[57] ABSTRACT o-cresolphthalein monophosphoric acid and salts thereof useful as substrates for alkaline phosphatase determinations are produced by reacting cresolphthalein with dibenzyl phosphite in the presence of carbon tetrachloride and an organic amine, hydrogenating the reaction product, recovering o-cresolphthalein monophosphoric acid from the hydrogenation product, and reacting the acid with bases to produce desired salts.

5 Claims, No Drawings

MONOPHOSPHATE SALT OF o-CRESOLPHTHALEIN

BACKGROUND OF THE INVENTION

This invention relates to cresolphthalein monophosphoric acid and salts thereof, a process for their production, and use of the salts as substrates for alkaline phosphatase determinations.

As depicted in Formula I and III, the cresol moiety is ortho-cresol. Accordingly, the term "cresolphthalein" appearing throughout the specification is to be construed as meaning ortho- or o-cresolphthalein.

Phenolphthalein monophosphates, as disclosed in U.S. Pat. Nos. 3,331,857 and 3,331,862, and thymolphthalein monophosphates hitherto have been employed advantageously as substrates for determining phosphatase. The amount of phenolphthalein or thymolphthalein released by enzymatic hydrolysis of the corresponding ester is proportional to the enzyme concentration. While both of the materials constitute popular substrates, they have certain limitations. Thus, phenolphthalein-based tests show some interference from bilirubin. Thymolphthalein monophosphate shows some lack of sensitivity to intestinal and placental phosphatase isoenzymes. Thymolphthalein monophosphate also is not suited for alkaline phosphatase determination by the kinetic method, described hereinafter.

It would be desirable to provide substrates for alkaline phosphatase determinations having the advantages of the prior phthalein monophosphates while minimizing or obviating the disadvantages thereof.

SUMMARY OF THE INVENTION

The invention provides a novel compound selected from the group consisting of cresolphthalein monophosphoric acid and salts thereof. The invention also provides a novel process for producing cresolphthalein monophosphoric acid which includes the steps of reacting cresolphthalein with dibenzyl phosphite in the presence of carbon tetrachloride and an organic amine, and hydrogenating the reaction product. Cresolphthalein monophosphoric acid is recovered from the hydrogenation product, and may be converted to a salt by reaction of the acid and a basic compound having a desired action.

The invention also provides a method for the determination of alkaline phosphatase enzyme which includes the steps of employing a salt of cresolphthalein monophosphoric acid as a subtrate for hydrolysis by alkaline phosphatase, and colorimetrically determining cresolphthalein liberated by the hydrolysis.

A subtrate prepared with a cresolphthalein monophosphate will yield a color produced by liberated cresolphthalein directly proportional to enzymatic activity upon hydrolysis by alkaline phosphatase, and phosphatase may be determined rapidly, either by the kinetic method or by the end point method. The sensitivity of cresolphthalein monophosphate to alkaline phosphatase isoenzymes is about equal to that of phenolphthalein monophosphate, while overcoming the lack of sensitivity to certain isoenzymes exhibited by thymolphthalein monophosphate, as noted above. The interference from bilirubin encountered in tests with phenolphthalein monophosphate is not as marked with cresolphthalein monophosphate.

The preparatory method of the invention constitutes an improvement over the methods disclosed in the aboveidentified patents when employed for the production of cresolphthalein monophosphate. The prior processes result in poor yields of cresolphthalein monophosphate and an impure product, whereas the product is obtained in improved yields and in high purity according to the present invention.

DESCRIPTION OF THE PREFERRED EMBODIMENTS

Cresolphthalein monophosphoric acid according to the invention has the following structural formula:

I

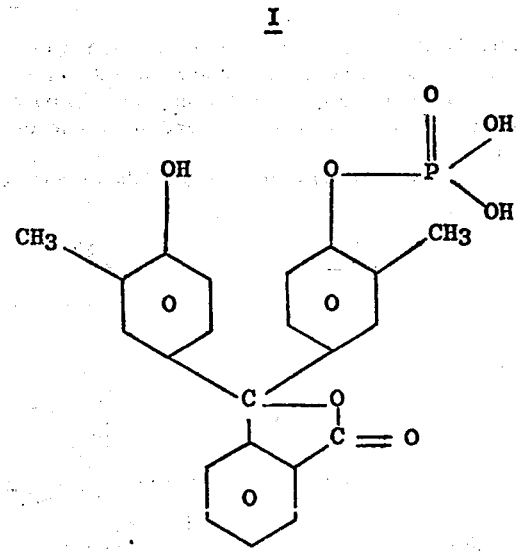

Cresolphthalein Monophosphoric Acid

Cresolphthalein monophosphoric acid is produced by phosphorylation of cresolphthalein as described hereinafter. The acid forms di- and tri-substituted salts by reaction with bases. Thus, for example, salts may be formed with alkali metal, alkaline earth metal, Group VIII metal, ammonium, and protonated organic amine cations. Illustrative metal cations include sodium, potassium, lithium, calcium, magnesium, barium, copper, iron, lead, and aluminum. Illustrative protonated organic amine cations include cyclohexylammonium, tetramethylethylenediammonium, ethanolammonium, and the like. The preferred salts are the alkali metal, alkaline earth metal, ammonium, and protonated organic amine salts.

The tri-substituted salts have the following structural formula:

II

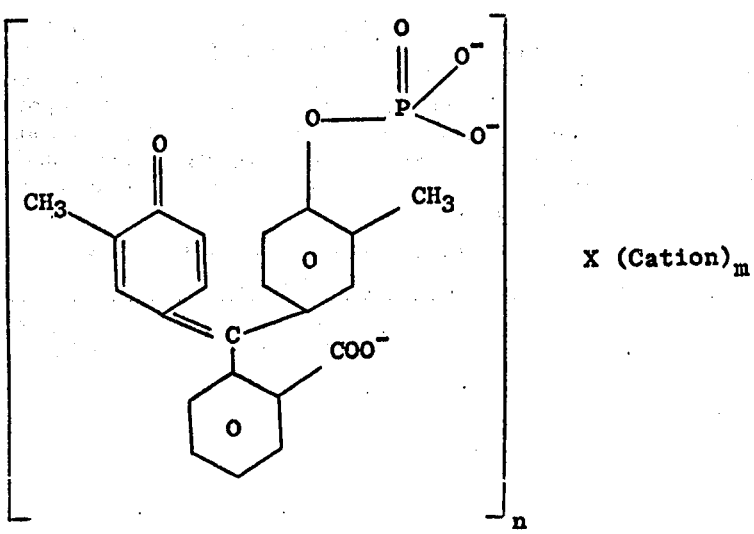

X (Cation)$_m$ wherein the cation X may be a metallic ion or ammonium, $n$ and $m$ are integers, and $m$(valence of X) = $3n$. It is further preferred that the metallic ion have a valence of 1 to 3, in which case $n$ and $m$ are integers from 1 to 3.

The di-substituted salts have the following structural formula:

III

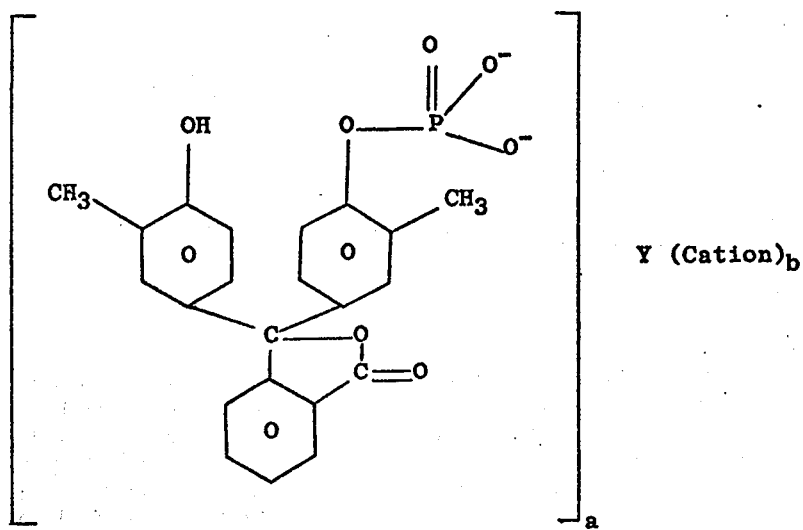

Y (Cation)$_b$ wherein the cation Y may be a metallic ion, ammonium, or a protonated organic amine, such as described above, $a$ and $b$ are integers, and $b$(valence of Y) = $2a$. It is preferred that the metallic ion have a valence of 1 to 3, in which case $a$ and $b$ are integers from 1 to 3. It will be noted upon comparison with formula I that cresolphthalein monophosphoric acid likewise exists in the lactone form, and may be represented by the same formula where the cation Y is hydrogen.

In the production of cresolphthalein monophosphoric acid according to the invention, cresolphthalein and dibenzyl phosphite are reacted in organic solvent solution in the presence of carbon tetrachloride and an organic base. Cresolphthalein is employed in slight molar excess, to provide an excess over the stoichiometric reaction quantity. The organic base is employed in a molar ratio to cresolphthalein of about 3:1. Cresolphthalein dibenzyl phosphate monoester is recovered as an oily intermediate product.

The ester is catalytically hydrogenated, to remove the benzyl groups in the form of toluene. The product of hydrogenation is cresolphthalein monophosphoric acid, which is obtained in a mixture with unreacted cresolphthalein. The two materials are separated in an aqueous alkaline medium, in which the cresolphthalein monophosphate which forms is soluble, while the cresolphthalein is insoluble and may be removed by filtration. The aqueous medium is acidified, and an oily layer of cresolphthalein monophosphoric acid separates and is recovered. The product is obtained in this manner in a high degree of purity.

Alkali metal, ammonium, and amine salts of cresolphthalein monophosphoric acid are prepared by direct reaction of corresponding bases with the acid. Disubstituted salts are prepared at relatively low alkaline pH, preferably about 7.5–10, and trisubstituted salts are prepared in strongly alkaline solution. Insoluble alkaline earth metal salts are prepared by reacting a soluble salt of an alkaline earth metal with a soluble cresolphthalein monophosphate, such as an alkali metal salt, and recovering the alkaline earth metal cresolphthalein monophosphate as a precipitate. Other cresolphthalein monophosphates may be prepared by analogous procedures.

In an alkaline phosphatase determination, blood serum or other biological material is added to a solution of a cresolphthalein monophosphate in an alkaline buffer. Cresolphthalein is released by enzymatic hydrolysis, and it is in its quinoid or colored state at the existing pH. The color is directly proportional to enzymatic activity (zero order kinetics with respect to substrate concentration and first order kinetics with respect to enzyme activity) to at least 400 International Units per liter, which is about ten times the upper limit of normal for human serum. The optical density of the solution is measured in the preferred range of 550 to 590 nanometers, more specifically, at 570 nanometers.

The following are specific examples of preferred products and methods or processes according to the invention. It will be understood that the invention is not limited to the examples, which are merely illustrative, or to the materials, proportions, conditions and procedures set forth therein.

EXAMPLE 1

Cresolphthalein monophosphoric acid is prepared by the following procedure:

34.64 g. (0.1M) of cresolphthalein is placed in a 1 liter round bottom flask equipped with a mechanical stirrer. 150 ml. of dry tetrahydrofuran is added and stirred until the cresolphthalein is dissolved. 400 ml. of carbon tetrachloride, 23.6 g. (0.09M) of dibenzyl phosphite, and 30 g. (0.3M) of triethylamine are added. In about 10 minutes, the reaction mixture warms up slightly and becomes turbid with the deposition of crystals of triethylamine hydrochloride.

The mixture is stirred overnight, filtered, and stripped to a thick oil in vacuo. The oil is dissolved in methanol and hydrogenated with hydrogen gas at atmospheric pressure and temperature in the presence of a palladium oxide catalyst, until the uptake of hydrogen ceases.

A volume of water equal to the volume of methanol used for solution is added, and the pH of the resulting oil suspension is adjusted to 7.3 with 50% sodium hydroxide. The methanol is removed by evaporation on a rotary evaporator. The remaining aqueous phase is filtered to separate unreacted cresolphthalein, which forms a precipitate. The filtrate is extracted three times with ethyl acetate, and the extracts are discarded.

The aqueous phase is adjusted to pH 4.0 by the dropwise addition of 1N hydrochloric acid thereto while stirring well, and then is allowed to stand in the refrigerator overnight. An oil separates from the aqueous phase, and the acqueous phase is separated by decantation. The oil is cresolphthalein monophosphoric acid in about 94% purity, and it is dissolved in methanol for preparing salts of the acid.

The disubstituted sodium, potassium, or lithium salt of cresolphthalein monophosphoric acid is produced by adjusting the pH of the methanol solution to 7.7 with a methanolic solution of the hydroxide of the metal. The solution is added to 10 volumes of diethyl ether while stirring vigorously, and stirring is continued for ten minutes. A precipitate of the alkali metal salt of cresolphthalein monophosphoric acid forms, and the precipitate is removed by filtration, air-dried, and sealed under vacuum. The product should be stored cold and dry.

The disubstituted ammonium salt or an amine salt of cresolphthalein monophosphoric acid is prepared in the foregoing manner, employing ammonium hydroxide or an amine hydroxide in methanol as the reactant with the acid.

To prepare the corresponding magnesium or calcium salt of cresolphthalein monophosphoric acid, a methanolic solution of the acid is adjusted to pH 7.5 with 1% methanolic sodium hydroxide. The calculated quantity of magnesium chloride hexahydrate or calcium chloride is added as a 5% aqueous solution while stirring. The magnesium or calcium cresolphthalein monophosphate precipitates from the solution and is separated by filtration.

EXAMPLE 2

Alkaline phosphatase in blood serum may be determined as follows:

A reagent is prepared by dissolving 400 mg. of cresolphthalein monophosphate disodium salt (prepared as described in Example 1) in 100 ml. of a 1 molar diethanolamine buffer containing 0.013 g. of magnesium chloride hexahydrate per 100 ml. at pH 10.1. The material is agitated to insure a complete solution.

In a kinetic method, 2.9 ml. of the reagent solution is transferred to a 1 cm. cuvet, and the cuvet is placed in the optical path of a spectrophotometer which is maintained at 30° C thermostatically. After establishment of thermal equilibrium, 0.1 ml. of human serum is added and mixed. The increase in optical density of the solution is read at 570 nanometers. The increase in optical density per unit of time is proportional to enzyme activity.

In an end point method, 1 ml. of the reagent is warmed to 30°C, and 0.1 ml. of human serum at 30°C is added. Exactly 10 minutes later, 5 ml. of a solution of 1% ethylenediaminetetraacetic acid adjusted to pH 10.1 is added. The optical density of the solution is measured at 570 nm., and compared to standards of cresolphthalein. The enzyme activity is proportional to color produced.

What is claimed is:

1. An o-cresolphthalein monophosphoric acid wherein the phosphoric acid moieties are optionally reacted with a hydroxide selected from the group consisting of alkali metal, alkaline earth metal, ammonium, cyclohexylammonium, tetramethylethylenediammonium, and ethanolammonium hydroxides.

2. Disodium o-cresolphthalein monophosphate.

3. A process which comprises reacting o-cresolphthalein in slight molar excess with dibenzyl phosphite in the presence of carbon tetrachloride and an organic amine base in a molar ratio to o-cresolphthalein of about 3:1, hydrogenating the reaction product with hydrogen gas in the presence of a palladium oxide catalyst, and recovering o-cresolphthalein monophosphoric acid from the hydrogenation product.

4. A process in accordance with claim 3, which further includes the steps of dissolving o-cresolphthalein monophosphoric acid in methanol, adding a methanolic solution of a hydroxide of a member of the group consisting of alkali metal, ammonium, cyclohexylammonium, tetramethylethylene diammonium and ethanolammonium hydroxides at a pH of 7.5 to 10, adding thereto an excess of diethyl ether and recovering a salt corresponding to the above added hydroxide.

5. A process in accordance with claim 3 comprising adjusting a methanolic solution of o-cresolphthalein monophosphoric acid to a pH of about 7.5 with methanolic sodium hydroxide, adding an aqueous solution of magnesium chloride hexahydrate or calcium chloride to form the corresponding magnesium or calcium salt of o-cresolphthalein monophosphoric acid and recovering the same.

* * * * *